(12) United States Patent
Trkovnik et al.

(10) Patent No.: US 6,291,518 B1
(45) Date of Patent: Sep. 18, 2001

(54) HYDROXY AND POLYHYDROXY DERIVATIVES OF COUMARIN, PREPARATION THEREOF AND ANTIVIRAL ACTION THEREOF

(75) Inventors: Mladen Trkovnik; Zrinka Ivezić, both of Zagreb (HR)

(73) Assignee: Pliva farmaceutska, kemijska, prehrambena i kozmeticka industrija, dionicko drustvo, Zagreb (HR)

( * ) Notice: Subject to any disclaimer, the term of this patent is extended or adjusted under 35 U.S.C. 154(b) by 0 days.

(21) Appl. No.: 09/476,133

(22) Filed: Jan. 3, 2000

Related U.S. Application Data

(62) Division of application No. 09/165,424, filed on Oct. 2, 1998, now Pat. No. 6,100,409.

(30) Foreign Application Priority Data

Oct. 2, 1997 (HR) .................................................. P970529A

(51) Int. Cl.[7] ..................... A61K 31/352; C07D 311/02; C07D 311/04

(52) U.S. Cl. .......................... 514/457; 549/284; 549/285; 549/286; 549/399; 549/400; 549/402

(58) Field of Search .................................... 549/284, 285, 549/286, 399, 400, 402; 514/457

(56) References Cited

U.S. PATENT DOCUMENTS 6,100,409 * 8/2000 Trkovnik et al. ..................... 549/284

OTHER PUBLICATIONS

Zhao et al, Chem. Alo. vol. 126 No. 98847, (1997), "Coumarin–Based Inhibitors of HIV Integrase", 1997.*

* cited by examiner

*Primary Examiner*—Alan L. Rotman
*Assistant Examiner*—Raymond Covington
(74) *Attorney, Agent, or Firm*—Connolly Bove Lodge & Hutz, LLP

(57) ABSTRACT

The present invention relates to novel hydroxy and polyhydroxy derivatives of coumarin fused with dialdehydes and aldehyde acids of the general formulae I, II, III and IV:

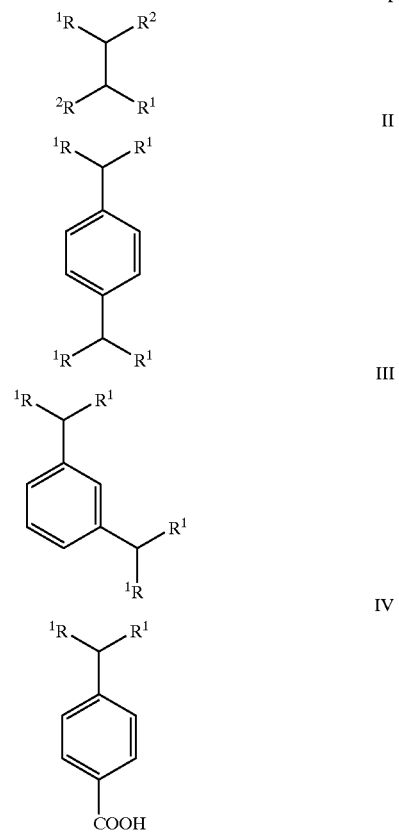

wherein
  $R^1=R^2$=4-hydroxycoumarin;
  $R^1=R^2$=4,7-dihydroxycoumarin;
  $R^1=R^2$=4,5,7-trihydroxycoumarin;
  $R^1$=4-hydroxycoumarin, $R^2$=—CH(OH)CH$_3$.

An object of the invention are also processes for the preparation of hydroxy and polyhydroxy derivatives of coumarin fused with dialdehydes and aldehyde acids, and the antiviral action thereof.

Novel hydroxy and polyhydroxy derivatives of coumarin according to the present invention exhibit antiviral action against HIV-1 virus.

10 Claims, No Drawings

HYDROXY AND POLYHYDROXY DERIVATIVES OF COUMARIN, PREPARATION THEREOF AND ANTIVIRAL ACTION THEREOF

CROSS REFERENCE TO RELATED APPLICATION

This application is a divisional of U.S. patent application Ser. No. 09/165,424 filed Oct. 2, 1998 now U.S. Pat. No. 6,100,409.

TECHNICAL FIELD

IPC: C07D 311/04

In investigations in the field of finding novel compounds having antiviral action against HIV-1 and HIV-2 viruses causing AIDS disease, some derivatives of 4-hydroxycoumarin, e.g. phenoprocoumon, showed a significant action (H. I. Skulnick et al., *J. Med. Chem.* 40 (1997) 1149). This invention gave a strong push to further investigations of novel hydroxycoumarin derivatives, which resulted in the synthesis of 3,3', 3", 3'"-(1,4-dimethylenephenyl)tetrakis[4-hydroxycoumarin] having the activity $IC_{50}=1.5$ $\mu$M (H. Zhao et al., *J. Med. Chem.* 40 (1997) 242).

It should especially be pointed out that derivatives of hydroxycoumarin may be used as oral non-peptide inhibitors of HIV-1 protease and integrase and some of the said derivatives have reached the first phase and the second phase of clinical trials.

On the basis of their earlier experiences the present inventors have prepared a series of novel hydroxy and polyhydroxy derivatives of coumarin in order to find still more active preparations with expressed action against HIV-1 and HIV-2 viruses.

The present invention relates to novel hydroxy and polyhydroxy derivatives of coumarin fused with dialdehydes and aldehyde acids of the general formulae I, II, III and IV:

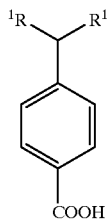

I

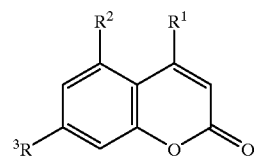

II

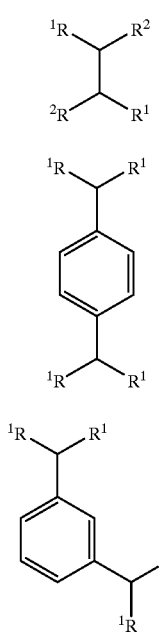

III

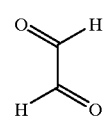

IV

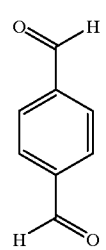

wherein $R^1=R^2$=4-hydroxycoumarin;

$R^1=R^2$=4,7-dihydroxycoumarin;

$R^1=R^2$=4,5,7-trihydroxycoumarin;

$R^1$=4-hydroxycoumarin, $R^2$=—CH(OH)CH$_3$.

Objects of the invention are also processes for the preparation of hydroxy and polyhydroxy derivatives of coumarin fused with dialdehydes and aldehyde acids, and the antiviral action thereof.

According to the present invention novel hydroxy and polyhydroxy derivatives of coumarin fused with dialdehydes and aldehyde acids of the general formulae I, II, III and IV are prepared starting from hydroxy- and polyhydroxycoumarin of the formula V

V wherein $R^1$=OH, $R^2=R^3$=H;

$R^1=R^3$=OH, $R^2$=H;

$R^1=R^2=R^3$=OH, by condensation reactions in ethanol or in glacial acetic acid wits dialdehydes and aldehyde acids of the formulae VI, VII, VIII and IX:

VI

VII

-continued

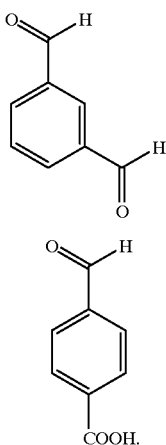

Novel hydroxy and polyhydroxy derivatives of coumarin according to the present invention exhibit antiviral action against HIV-1 virus.

The invention is illustrated by the following Examples, which in no way limit the scope thereof.

EXAMPLE 1

3,3',3'',3'''-ethylenetetrakis[4-hydroxycoumarin]

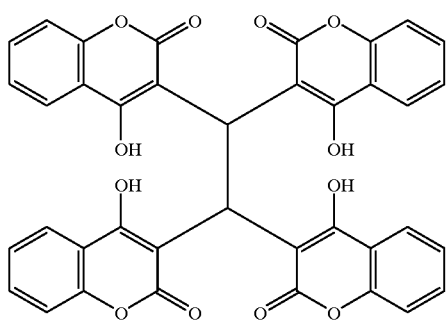

4-hydroxycoumarin (10.00 g; 61.7 mmol) was dissolved in glacial acetic acid (70.0 ml) and to this solution a 30% aqueous glyoxal solution (2.75 ml; 17.0 mmol) was added. The reaction mixture was heated at boiling temperature for 5 hours. Upon cooling a yellow precipitate (7.21 g; 70%) was obtained and it was recrystallized from glacial acetic acid. M.p. 298–300° C.

Analysis:

| calculated for $C_{38}H_{22}O_{12}$: | C = 68.06; H = 3.31. |
|---|---|
| found: | C = 68.33; H = 3.12. |

FABMS: m/z: 671 (M$^+$)

IR (KBr): v/cm$^{-1}$: 3447 (br); 1719; 1637; 1607; 761.

EXAMPLE 2

3,4-di(4-hydroxycoumarin)-hexane-2,5-diol

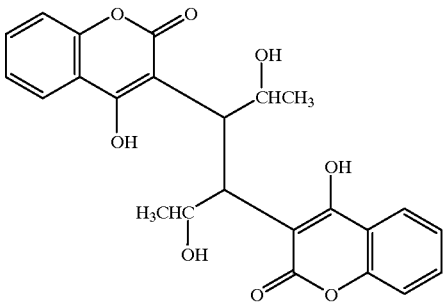

4-hydroxycoumarin (10.00 g; 61.7 mmol) was dissolved in 96% ethanol (50.0 ml) and to this solution a 30% aqueous glyoxal solution (2.75 ml; 17.0 mmol) was added. The reaction mixture was heated at boiling temperature for 15 minutes. The obtained white precipitate was filtered in vacuo and washed several times with hot 96% ethanol (6.05 g; 58%). M.p. 309–310° C.

Analysis:

| calculated for $C_{24}H_{22}O_8$: | C = 65.75; H = 5.06. |
|---|---|
| found: | C = 65.64; H = 5.04. |

FABMS: m/z: 439 (M$^+$)

IR (KBr): v/cm$^{-1}$: 3389 (br); 2981; 1721; 1669; 1640; 1236; 761.

EXAMPLE 3

3,3',3'',3'''-ethylenetetrakis[4,7-dihydroxycoumarin]

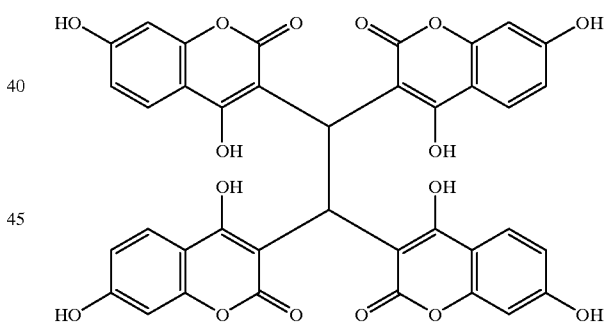

To a solution of 4,7-dihydroxycoumarin (2.50 g; 14.0 mmol) in absolute ethanol (10.0 ml) a 30% aqueous glyoxal solution (0.65 ml; 3.86 mmol) was added. The reaction mixture was heated at boiling temperature for 4 hours under discharging ethanol during the reaction, upon cooling it was left overnight at −13° C. and the obtained light yellow precipitate was filtered in vacuo (1.20 g; 47%). It was recrystallized from N,N-dimethylformamide/glacial acetic acid mixture (1:1). M.p. >300° C.

Analysis:

| calculated for $C_{38}H_{22}O_{16}$: | C = 62.13; H = 3.02. |
|---|---|
| found: | C = 62.39; H = 2.65. |

FABMS: m/z: 735 (M$^+$)

IR (KBr): v/cm$^{-1}$: 3435 (br); 1720; 1630; 1601; 760.

EXAMPLE 4

3,3',3'',3'''-ethylenetetrakis[4,5,7-trihydroxycoumarin]

XIII

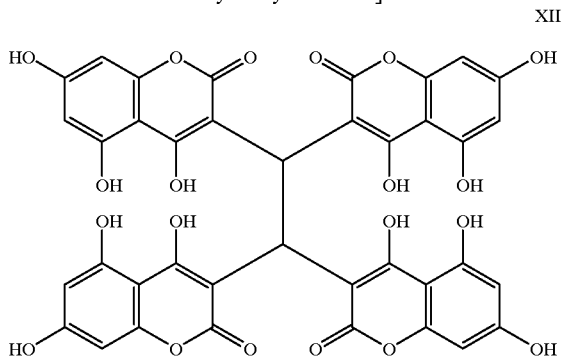

To a solution of 4,5,7-trihydroxycoumarin (2.00 g; 10.3 mmol) in absolute ethanol (10.0 ml) a 30% aqueous glyoxal solution (0.50 ml; 2.84 mmol) was added. The reaction mixture was heated at boiling temperature for 30 minutes and then evaporated to one third of the volume. To the residue in a flask a low-boiling petroleum ether was added and it was stirred for one hour at room temperature, whereat the gelatinous solution turned into a fine crystalline orange brown precipitate (1.44 g; 70%). It was recrystallized from a 96% ethanol/glacial acetic acid mixture (1:1). M.p. >300° C.

Analysis:

| | |
|---|---|
| calculated for $C_{38}H_{22}O_{20} \times H_2O$: | C = 55.89; H = 2.96. |
| found: | C = 55.53; H = 3.32. |

FABMS: m/z: 799 (M$^+$)

IR (KBr): $\nu$/cm$^{-1}$: 3423 (br); 2959; 1618; 1299; 1157; 761.

EXAMPLE 5

3,3',3'',3'''-(1,4-dimethylenephenyl)tetrakis[4,5,7-trihydroxycoumarin]

XIV

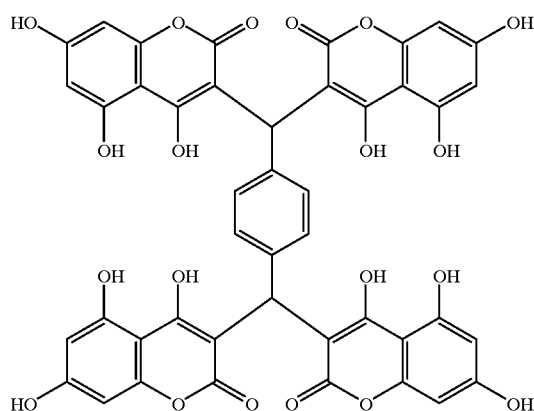

To a solution of 4,5,7-trihydroxycoumarin (3.00 g; 15.5 mmol) in 96% ethanol (15.0 ml) terephthaldialdehyde (0.57 g; 4.26 mmol) was added. The reaction mixture was heated at boiling temperature for 30 minutes and abundant gelatinous precipitate was formed. The obtained precipitate was filtered in vacuo and then transferred to a flask, into which also diisopropyl ether (30.0 ml) was added under stirring for one hour at room temperature. The obtained orange red precipitate was filtered off and dried (2.92 g; 86%). M.p. 228–230° C.

Analysis:

| | |
|---|---|
| calculated for $C_{44}H_{26}O_{20}$: | C = 60.42; H = 3.00. |
| found: | C = 60.37; H = 2.76. |

FABMS: m/z: 875 (M$^+$)

IR(KBr): $\nu$/cm$^{-1}$: 3380 (br); 1648; 1622; 1601; 1260; 760.

EXAMPLE 6

3,3',3'',3'''-(1,3-dimethylenephenyl)tetrakis[4,5,7-trihydroxycoumarin]

XV

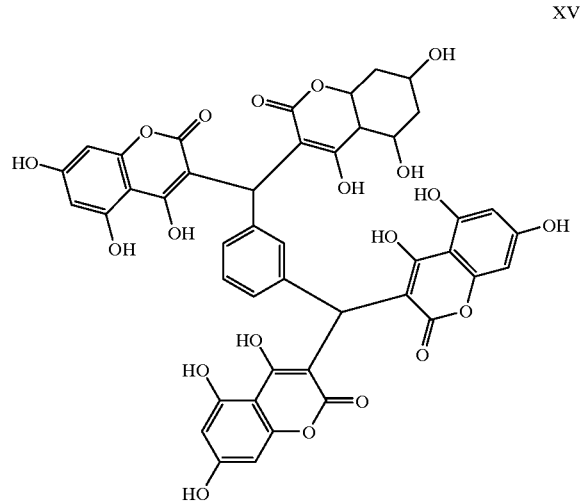

To a solution of 4,5,7-trihydroxycoumarin (3.00 g; 15.5 mmol) in 96% ethanol (1.5.0 ml) isophthaldialdehyde (0.57 g; 4.26 mmol) was added. The reaction mixture was heated at boiling temperature for 3.5 hours and abundant gelationous precipitate was formed. The obtained precipitate was filtered in vacuo and then transferred to a flask, into which also diisopropyl ether (150.0 ml) was added under stirring for 30 minutes at room temperature and then for another hour under reflux. The red brown precipitate obtained by cooling was filtered off and dried (3.33 g; 98%). M.p. >300° C.

Analysis:

| | |
|---|---|
| calculated for $C_{44}H_{26}O_{20}$: | C = 60.42; H = 3.00. |
| found: | C = 60.48; H = 3.04. |

FABMS: m/z: 875 (M$^+$)

IR(KBr): $\nu$/cm$^{-1}$: 3374 (br); 1640; 1610; 1597; 1249; 761.

EXAMPLE 7

3,3'-(4-carboxybenzylidene)bis[4,7-dihidroxycoumarin]

XVI

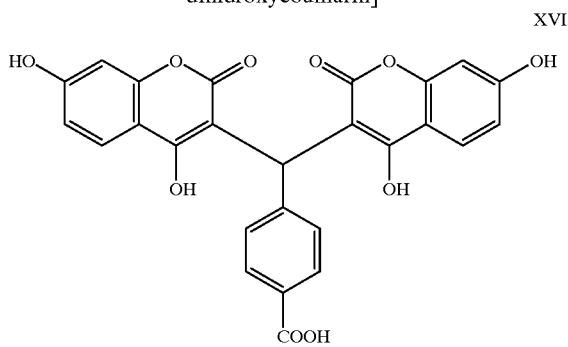

To a solution of 4,7-dihidroxycoumarin (4.00 g; 22.5 mmol) in 96% ethanol (50.0 ml) terephthalaldehyde acid (1.86 g; 1.24 mmol) was added. The reaction mixture was heated at boiling temperature for 8 hours. After cooling to room temperature the reaction mixture was evaporated to one half of its volume and left overnight at −13° C. After filtering in vacuo a pale yellow precipitate (2.84 g; 52%) was obtained and recrystallized from 20% ethanol. M.p. 239–242° C.

Analysis:

| | |
|---|---|
| calculated for $C_{26}H_{16}O_{10} \times H_2O$: | C = 61.66; H = 3.58. |
| found: | C = 61.32; H = 3.56. |

FABMS: m/z: 489 (M$^+$)

IR(KBr): ν/cm$^{-1}$: 3323 (br); 1697; 1620; 1571; 1253; 760.

EXAMPLE 8

3,3'-(4-carboxybenzylidene)bis[4,5,7-trihidroxycoumarin]

XVII

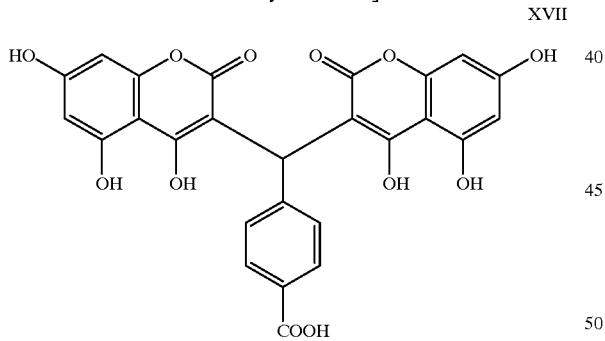

To a solution of 4,5,7-trihidroxycoumarin (2.00 g; 10.3 mmol) in 96% ethanol (10.0 ml) terephthalaldehyde acid (0.85 g; 5.67 mmol) was added. The reaction mixture was heated at boiling temperature for 12 hours. After cooling to room temperature the reaction mixture was evaporated to one half of its volume and left overnight at −13° C. and then water (20.0 ml) was added under stirring and under cooling with ice from exterior. The obtained precipitate was filtered in vacuo (1.80 g; 67%). M.p. 278–280° C.

Analysis:

| | |
|---|---|
| calculated for $C_{26}H_{16}O_{12}$: | C = 60.01; H = 3.10. |
| found: | C = 59.73; H = 3.34. |

FABMS: m/z: 521 (M$^+$)

IR(KBr): ν/cm$^{-1}$: 3420 (br); 1697; 1662; 1609; 1285; 760.

What is claimed is:

1. Hydroxy and polyhydroxy derivatives of coumarin fused with dialdehydes and aldehyde acids of the formulae I, II, III and IV:

I

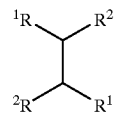

II

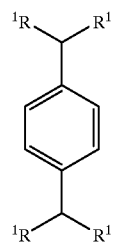

III

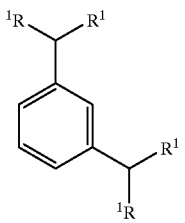

IV

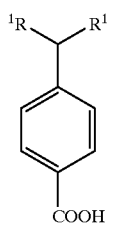

wherein $R^1=R^2$=4-hydroxycoumarin;

$R^1=R^2$ 4,7-dihydroxycoumarin;

$R^1=R^2$=4,5,7-trihydroxycomarin;

$R^1$=4-hydroxycoumarin, $R^2$=—CH(OH)CH$_3$.

2. Compound of the formula I according to claim 1, characterized in that $R^1=R^2$=4-hydroxycoumarin.

3. Compound of the formula I according to claim 1, characterized in that $R^1$=4-hydroxycoumarin, $R^2$=—CH(OH)CH$_3$.

4. Compound of the formula I according to claim 1, characterized in that $R^1=R^2$=4,7-dihydroxycoumarin.

5. Compound of the formula I according to claim 1, characterized in that $R^1=R^2$=4,5,7-trihydroxycoumarin.

6. Compound of the formula III according to claim 1, characterized in that $R^1$=4,5,7-trihydroxycoumarin.

7. Compound of the formula IV according to claim 1, characterized in that $R^1$=4,7-dihydroxycoumarin.

8. Compound of the formula IV according to claim 1, characterized in that $R^1$=4,5,7-trihydroxycoumarin.

9. Process for the preparation of compounds of the formula I, II, III, IV according to claim 1, characterized in that they are obtained from the compounds of the general formula V

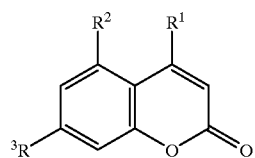

V wherein $R^1$=OH, $R^2$=$R^3$=H, $R^1$=$R^3$=OH, $R^2$=H, $R^1$=$R^2$=$R^3$=OH, by condensation reactions in ethanol or glacial acetic acid with dialdehydes or aldehyde acids of the formulae VI, VII, VIII and IX

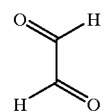

VI

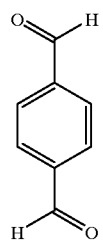

VII

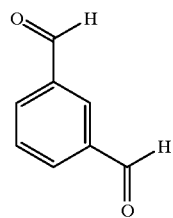

VIII

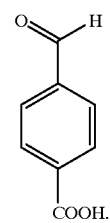

IX

10. Hydroxy and polyhydroxy derivatives of coumarin fused with dialdehydes and aldehyde acids of the formulae I, II, III and IV, characterized in that they exhibit an antiviral action against HIV-1 virus.

* * * * *